US008921754B2

(12) United States Patent
Frach (10) Patent No.: US 8,921,754 B2
(45) Date of Patent: Dec. 30, 2014

(54) ADVANCED TEMPERATURE COMPENSATION AND CONTROL CIRCUIT FOR SINGLE PHOTON COUNTERS

(75) Inventor: Thomas Frach, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 700 days.

(21) Appl. No.: 13/148,055

(22) PCT Filed: Feb. 5, 2010

(86) PCT No.: PCT/IB2010/050539
§ 371 (c)(1),
(2), (4) Date: Aug. 5, 2011

(87) PCT Pub. No.: WO2010/100574
PCT Pub. Date: Sep. 10, 2010

(65) Prior Publication Data
US 2011/0291017 A1  Dec. 1, 2011

Related U.S. Application Data

(60) Provisional application No. 61/157,923, filed on Mar. 6, 2009.

(51) Int. Cl.
| H01L 31/00 | (2006.01) |
| H03G 3/20 | (2006.01) |
| G01T 1/40 | (2006.01) |
| G01T 1/20 | (2006.01) |
| G01T 7/00 | (2006.01) |

(52) U.S. Cl.
CPC .............. *G01T 1/40* (2013.01); *G01T 1/2018* (2013.01); *G01T 7/005* (2013.01)

USPC .................................. 250/214 AG; 250/214.1

(58) Field of Classification Search
CPC ..................................................... H04B 10/6911
USPC ................................. 250/214 AG, 214.1, 214
See application file for complete search history.

(56) References Cited

U.S. PATENT DOCUMENTS 4,599,527 A   7/1986  Beaudet et al.
6,222,660 B1 *  4/2001  Traa .............................. 398/213
(Continued)

OTHER PUBLICATIONS

Scafe, R., et al.; Scintillation crystal readout by multi-APD for event localization; 2006; Nuclear Instruments and Methods in Physics Research; A 569:180-184.

(Continued)

Primary Examiner — David J Makiya
Assistant Examiner — Kenneth J Malkowski (57) ABSTRACT

A PET scanner (10) includes a ring of detector modules (16) encircling an imaging region (18). Each of the detector modules includes one or more sensor avalanche photodiodes (APDs) (34) that are biased in a breakdown region in a Geiger mode. The sensor APDs (34) output pulses in response to light from a scintillator corresponding to incident photons. A reference APD (36) also biased in a breakdown region in a Geiger mode is optically shielded from light and outputs a voltage that is measured by an analog to digital converter (44). Based on the measurement, a bias control feedback loop (42) directs a variable voltage generator (48) to adjust a bias voltage applied to the APDs (34, 36) such that a difference (86) between a voltage of a breakdown pulse (68) and a preselected logic voltage level (70) is minimized.

19 Claims, 7 Drawing Sheets

(56) References Cited

U.S. PATENT DOCUMENTS

| | | |
|---|---|---|
| 7,155,133 B2 | 12/2006 | Stewart et al. |
| 7,224,908 B2 * | 5/2007 | Alwan et al. .................. 398/197 |
| 7,332,702 B2 | 2/2008 | Nishiyama |
| 7,402,788 B2 | 7/2008 | McVey |
| 2001/0023944 A1 | 9/2001 | Maruyama et al. |
| 2002/0195545 A1 | 12/2002 | Nishimura et al. |
| 2008/0156993 A1 * | 7/2008 | Weinberg et al. ........ 250/363.03 |
| 2008/0203309 A1 * | 8/2008 | Frach et al. .................. 250/362 |
| 2008/0303524 A1 | 12/2008 | Schon et al. |

OTHER PUBLICATIONS

Horste, J.; Adjusting APD power-supply voltage with DACs and variable resistors; Sep. 2007; Lightwave; http://lw.pennet.com/display_article/305881/13/ARTCL/none/none/1.

* cited by examiner

ADVANCED TEMPERATURE COMPENSATION AND CONTROL CIRCUIT FOR SINGLE PHOTON COUNTERS

CROSS REFERENCE TO RELATED APPLICATIONS

This application claims the benefit of U.S. provisional application Ser. No. 61/157,923 filed Mar. 6, 2009, which is incorporated herein by reference.

The following relates to the diagnostic imaging arts. It finds particular application in conjunction with radiation detectors for nuclear medical imagers employing radiation transmission or radiopharmaceuticals, such as single photon emission computed tomography (SPECT) imagers, positron emission tomography (PET) imagers, planar x-ray imagers, and the like, and will be described with particular reference thereto. It will be appreciated that the invention may also be applicable to other radiation imaging modalities, and in systems and methods employing radiation detectors such as astronomy and airport luggage screening.

In SPECT, a radiopharmaceutical is administered to an imaging subject, and one or more radiation detectors, commonly called gamma cameras, are used to detect the radiopharmaceutical via radiation emission caused by radioactive decay events. Typically, each gamma camera includes a radiation detector array and a honeycomb collimator disposed in front of the radiation detector array. The honeycomb collimator defines a linear or small-angle conical line of sight so that the detected radiation comprises projection data. If the gamma cameras are moved over a range of angular views, for example over a 180° or 360° angular range, then the resulting projection data can be reconstructed using filtered back-projection, expectation-maximization, or another imaging technique into an image of the radiopharmaceutical distribution in the imaging subject. Advantageously, the radiopharmaceutical can be designed to concentrate in selected tissues to provide preferential imaging of those selected tissues.

In PET, a radiopharmaceutical is administered to the imaging subject, in which the radioactive decay events of the radiopharmaceutical produce positrons. Each positron interacts with an electron to produce a matter/anti-matter annihilation event that emits two oppositely directed gamma rays. Using coincidence detection circuitry, an array of radiation detectors surrounding the imaging subject detects the coincident oppositely directed gamma ray events corresponding to the positron-electron annihilation. A line of response (LOR) connecting the two coincident detections contains the position of the positron-electron annihilation event. Such lines of response are analogous to projection data and can be reconstructed to produce a two- or three-dimensional image. In time-of-flight PET (TOF-PET), the small time difference between the detection of the two coincident γ ray events is used to localize the annihilation event along the LOR.

In planar x-ray imaging, a radiation source irradiates a subject, and a radiation detector array disposed on the opposite side of the subject detects the transmitted radiation. Due to attenuation of radiation by tissues in the imaging subject, the detected radiation provides a two-dimensional planar representation of bones or other hard, radiation-absorbing structures in the imaging subject. Such transmission-based imaging is improved upon in computed tomography (CT) imaging, in which the radiation source is revolved around the imaging subject to provide transmission views or projection data over an extended angular range, for example over a 180° or 360° span of angular views. Using filtered back-projection or another image reconstruction technique, this radiation projection data is reconstructed into a two- or three-dimensional image representation.

SPECT, PET, and other radiation-based medical imaging share a common need for compact and robust radiation detector modules. In the past, SPECT and PET radiation detector modules have typically consisted of an array of photomultiplier tubes (PMT's) optically coupled with scintillator crystals. The scintillator crystal absorbs the radiation particle and converts it into a light burst which is measured by the photomultiplier tubes. Photomultiplier tubes provide high detection and gain ($\sim10^6$) characteristics but they are bulky, fragile, require high voltages, and are very sensitive to magnetic fields. In some radiation detection systems, the photomultiplier tubes have been replaced by photodiodes that produce an analog signal proportional to the intensity of the light bursts. Even though photodiodes offer a cost-effective, low voltage alternative to photomultiplier tubes in high light situations, they do not provide the adequate gain in low light (low gamma ray flux) sensing applications, thus leading to poor signal-to-noise ratios.

To address these difficulties, silicon photomultiplier (SiPM) detectors have been developed that incorporate the high gain and stability of photomultiplier tubes along with the cost-effective, low voltage nature of the photodiodes. SiPM detectors use an array of small avalanche photodiodes (APDs) that are each optically coupled to a corresponding scintillation crystal. The APDs are biased in a breakdown region. In this region, the APDs become sensitive to single carriers, such as may be caused by an incident photon. These carriers, electrons and/or holes, can also be thermally generated, thus leading to dark counts that cause noise. Both electrons and holes can initiate the breakdown of the diode, thereby producing a strong output signal. In analog SiPMs, the output signal consists of the cumulative charge of a large number of passively quenched diodes. In contrast, digital SiPMs detect breakdown events individually based on voltage pulses that are digitized by logic gates and counted by digital counters that are located approximate to the APDs.

In digital Geiger-mode, APDs break down in response to a photon of light from a radiation event in the corresponding scintillation crystal and produce an output pulse. The output pulse functioning as binary 1's are counted to determine the number of photons generated by the radiation event striking the corresponding scintillator. This photon count corresponds to the energy of the detected radiation event.

While sensitive to individual photon events, breakdown voltage of each APD is affected by various ambient factors, such as magnetic fields and temperature. Drift of the breakdown voltage leads to a corresponding change of an excess voltage. Photon detection is affected by changes in excess voltage because: (1) the excess voltage determines the field strength inside the device, thus leading to a drift of the photon detection probability, and (2) the charge pulse produced during breakdown is proportional to the product of the diode capacitance and the excess voltage. Analog SiPMs, which count detected photons as a measured charge signal, are affected by both factors and become very sensitive to ambient conditions. The dark current rate (DCR) is doubled approximately every 8° C. To reduce the DCR of the sensor and avoid errors due to variations in the APDs, cooling can help, but even with cooling, temperature fluctuations can occur.

The present application contemplates a new and improved nuclear imaging detector apparatus and method that overcomes the above-referenced problems and others.

In accordance with one aspect, a radiation detector module is provided. A plurality of detector pixels each have a scintillator optically coupled to at least one sensor photodiode operated in a Geiger mode. At least one reference photodiode is shielded from light and is operated under the same conditions as the at least one sensor photodiode. The module includes a control circuit that measures a breakdown voltage across the reference photodiode, and adjusts a bias voltage across the at least one reference photodiode and the at least one sensor photodiode. This brings the dark current pulses generated by the at least one reference photodiode into substantial equality with the characteristic logic voltage level.

In accordance with another aspect, a method of compensating for drift in a sensitivity of a portion of a radiation detector array is provided. A bias voltage is applied to a plurality of sensor photodiodes and a parallel connected reference photodiode. The reference photodiode is covered with an opaque covering, preventing it from receiving light from an associated scintillator. The bias voltage biases the photodiodes to a Geiger mode, sensitive to single photons. Following breakdown of the reference photodiode, a breakdown voltage of the reference photodiode is measured. A difference between a value of a digitized pulse from the reference photodiode and a logic voltage level is determined. The bias voltage is adjusted to minimize the difference.

One advantage resides in improved breakdown voltage control for avalanche photodiodes operated in the Geiger mode.

Another advantage lies in compensation for several ambient factors that affect the sensitivity of the photodiodes.

Another advantage lies in the flexibility to be used in either analog or digital systems.

Another advantage lies in the freedom of the system builder to relax requirements on temperature stabilization without compromising system performance.

Still further advantages and benefits will become apparent to those of ordinary skill in the art upon reading and understanding the following detailed description.

The present application may take form in various components and arrangements of components, and in various steps and arrangements of steps. The drawings are only for purposes of illustrating the preferred embodiments and are not to be construed as limiting the present application.

Figure 1:
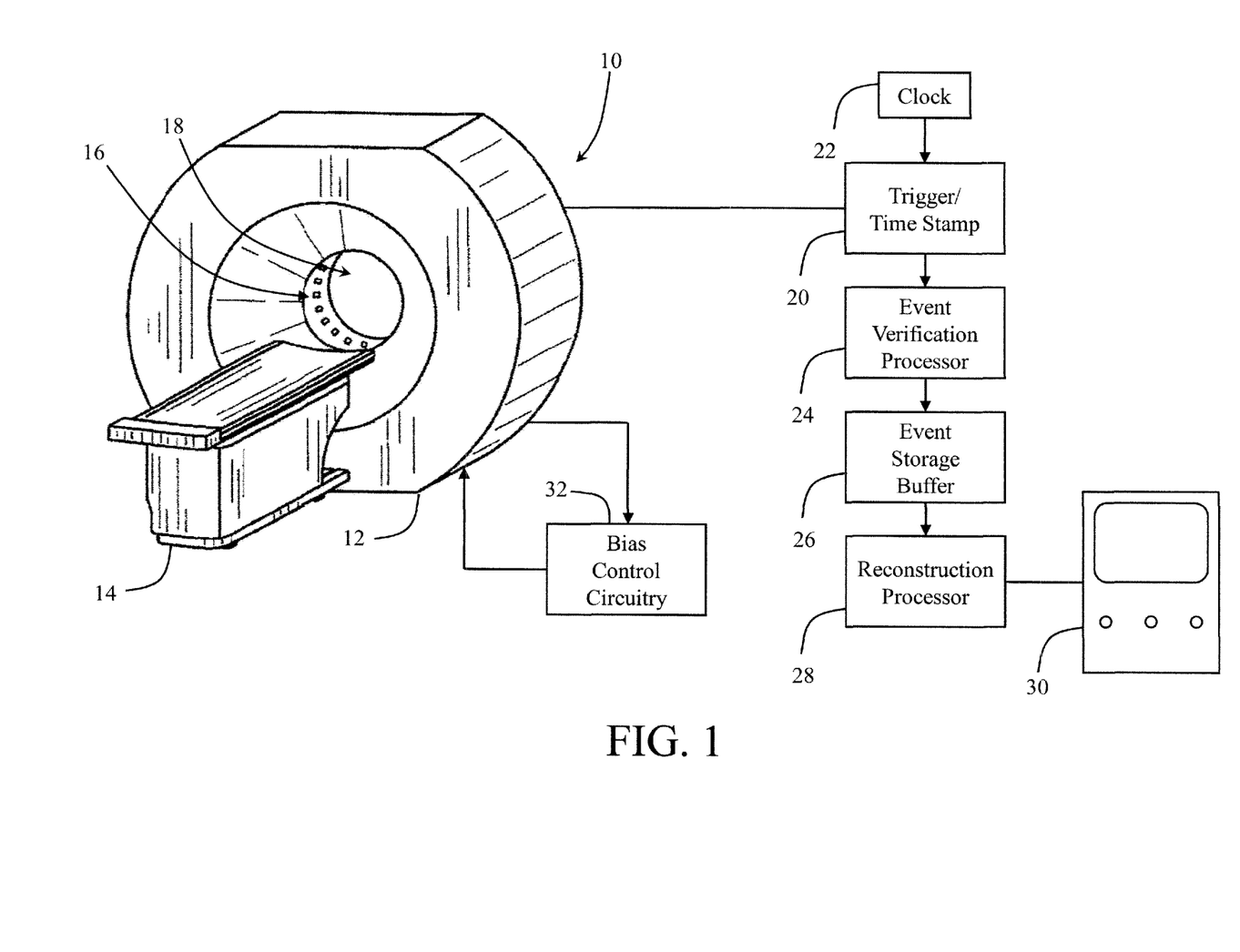
FIG. 1 is a diagrammatic illustration of a nuclear imaging scanner in accordance with the present application.

With reference to FIG. 1, a diagnostic imaging device 10 includes a housing 12 and a subject support 14. Enclosed within the housing 12 is a detector array. The detector array includes a plurality of individual detector modules 16. The array may include hundreds or thousands of radiation detector modules 16. While one particular embodiment is described with reference to a positron emission tomography (PET) scanner, it is to be understood that the present application is also useful in other medical applications, such as single photon emission computed tomography (SPECT) as well as x-ray astrophysics, gamma ray telescopes, radiography, security, and industrial applications. Generally, the present application finds use in imaging x-rays, gamma rays, or charged particles with high energy and spatial resolution. The array is arranged so that detector elements 16 are disposed adjacent to an imaging region 18 and oriented to receive radiation from the imaging region 18. The subject support 14 is movable in to and out of the imaging region 18. This allows the detector array to be sensitive to multiple views of the subject, without having to reposition the subject on the support 14. The detector array can be a ring of detectors 16, multiple rings, one or more discrete flat or arced panels, or the like.

In PET, pairs of gamma rays are produced by a positron annihilation event in the imaging region and travel in approximately opposite directions. Such an event may be produced from the nuclear decay of $^{82}$Rb. These gamma rays are detected as pairs, with a slight time difference (on the order of nanoseconds or fractions thereof) between detections if one gamma ray travels farther to reach a detector than the other. Accordingly, in PET scanners, the detector arrays typically encircle the imaging region.

Before the PET scan commences, a subject is injected with a radiopharmaceutical. In one common exam, the radiopharmaceutical contains a radioactive element, such as $^{82}$Rb, coupled to a tag molecule. The tag molecule is associated with the region to be imaged, and tends to gather there through body processes. For example, rapidly multiplying cancer cells tend to expend abnormally high amounts of energy duplicating themselves. The radiopharmaceutical can be linked to a molecule, such as glucose, or an analog thereof, that a cell typically metabolizes to create energy, which gathers in such regions and appear as "hot spots" in the image. Such a tag is also useful in cardiac perfusion imaging, since the heart expends relatively large amounts of energy. Other techniques monitor tagged molecules flowing in the circulatory system. In such a technique, it is beneficial to tag a molecule that is not quickly absorbed by tissues of the body.

When a gamma ray strikes the detector array, a time signal is generated. A triggering processor 20 monitors each detector 16 for an energy spike, e.g., integrated area under the pulse, characteristic of the energy of the gamma rays generated by the radiopharmaceutical. The triggering processor 20 checks a clock 22 and stamps each detected gamma ray with a time of leading edge receipt stamp. The time stamp, energy estimate and position estimation is first used by an event verification processor 24 to determine if the event data is valid, e.g., if the pair of events are coincident, have the proper energy, and the like. Accepted pairs define lines of response (LORs). Because gamma rays travel at the speed of light, if detected gamma rays arrive more than several nanoseconds apart, they probably were not generated by the same annihilation event and are usually discarded. Timing is especially important in time of flight PET (TOF-PET), as the minute difference in substantially simultaneous coincident events is used to further localize the annihilation event along the LOR. As the temporal resolution of events becomes more precise, so too does the accuracy with which an event can be localized along its LOR.

LORs are stored in an event storage buffer 26. In one embodiment, the LORs are stored in a list-mode format. That is, the events are stored in temporal order with time indicators periodically inserted. Alternatively, the events can be individually time stamped. A reconstruction processor 28 reconstructs all or a portion of the LORs into an image representation of the subject using filtered backprojection or other appropriate reconstruction algorithms. The reconstruction can then be displayed for a user on a display device 30, printed, saved for later use, and the like.

Each detector module 16 includes a plurality of photodiodes in one embodiment. While operating the photodiodes in Gieger mode, a reverse bias voltage is applied to allow the photodiodes to be sensitive to single photons of light generated by associated scintillation crystals optically coupled to the photodiodes. The scintillators are selected to provide high stopping power for incumbent radiation with rapid temporal decay of the scintillation burst. Some suitable scintillator materials include LSO, LYSO, MLS, LGSO, LaBr, CsI(Ti), and mixtures thereof. The bias voltage is applied such that the photodiodes produce an avalanche current when struck by the scintillated photons, earning them the moniker avalanche photodiodes (APDs). The optimum bias voltage is sensitive to multiple factors, such as temperature, pressure, ambient light, and the like. Bias voltage control circuitry 32 monitors the detector modules 16 and adjusts the applied bias voltage as conditions dictate.

Figure 2:
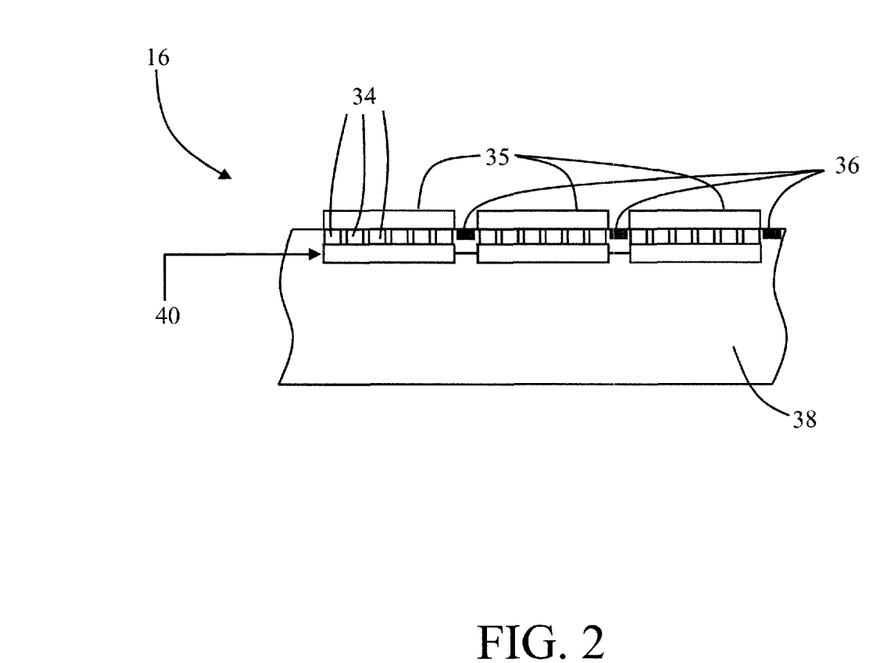
FIG. 2 depicts a cutaway view of a detector module, in accordance with the present application.

With reference to FIG. 2, a pixelated detector module 16 includes at least one sensor APD 34, more particularly one or more SiPMs each including an array of the APDs 34, optically coupled to a scintillation crystal 35. Additionally, each module 16 also includes at least one reference detector 36, such as a reference APD. The reference APDs 36 are covered with an opaque enclosure, such as a metal cap, to prevent light (ambient light or scintillation bursts) from reaching the reference APDs 36. The reference APDs 36 are placed among the sensor APDs 34, as it is desirable to have the sensor APDs 34 and the reference APDs 36 operating in the same environment, aside from the reception of light. In the illustrated embodiment, the sensor APDs 34 and reference APDs 36 are formed on a common substrate 38.

A digital circuitry layer 40 is electronically connected to the sensor photodiodes 34 and the reference photodiodes 36. The digital circuitry layer 40 includes circuitry that collects and outputs photon detection specific information such as radiation detector module identification, pixel identification, timestamps, and photon counts. The digital circuitry may also include digital biasing circuitry, digital triggering circuitry, and readout circuitry. The bias control circuitry 32 can be located in the digital circuit layer 40. Alternately, the bias control circuitry 32 can be located on a separate chip or die.

Figure 3:
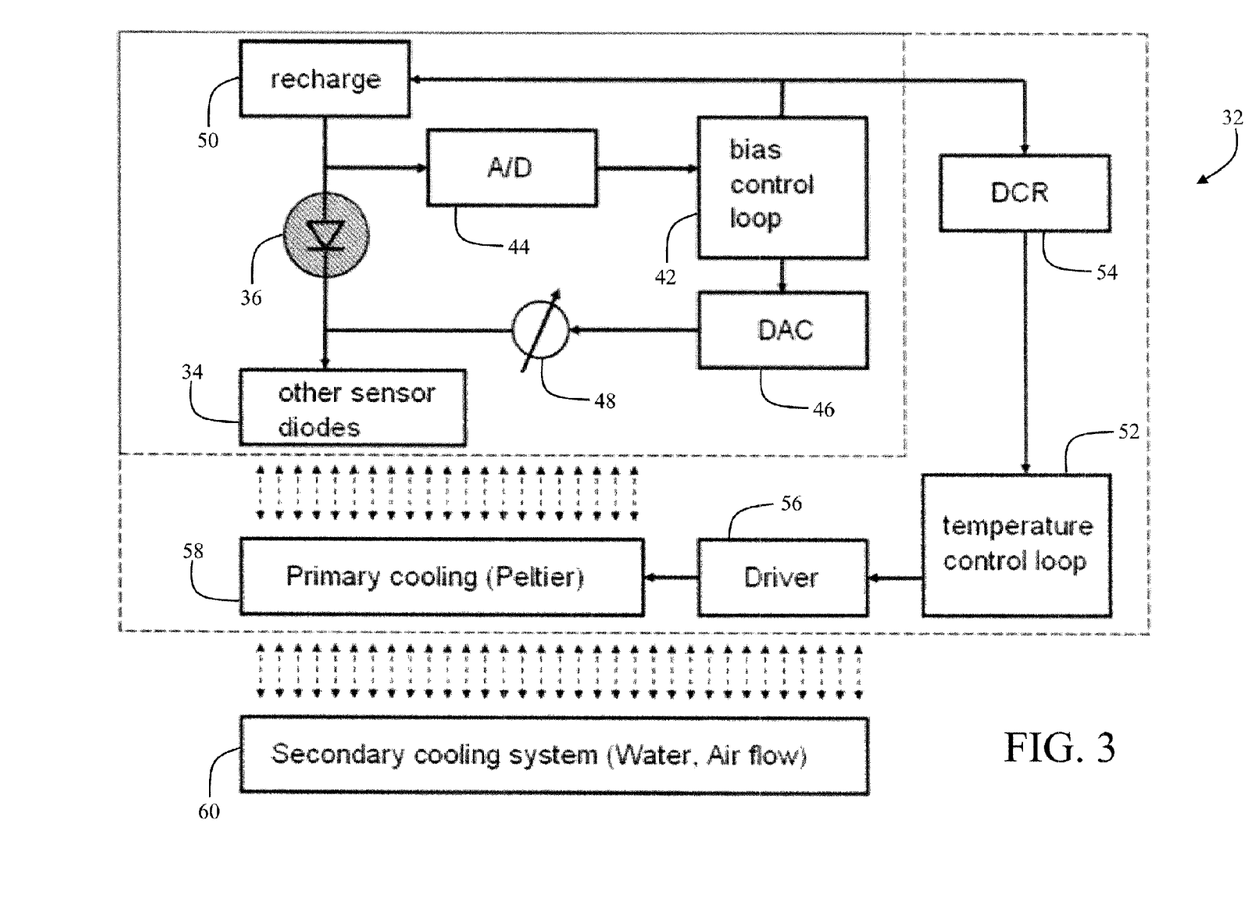
FIG. 3 is a flow diagram depicting bias control and temperature control feedback loops.

With reference now to FIG. 3, the bias control circuitry 32 includes a first, bias control feedback loop 42. Instead of detecting photo-generated electron-hole pairs, the reference APD 36 detects thermally generated electron-hole pairs or dark current. Thermally generated electron-hole pairs are created by generation-recombination processes within the semiconductor and can trigger an avalanche current in the absence of scintillated photons, producing noise in the system. The bias voltage across the APDs 34, 36 can be adjusted to make the APDs 34, 36 more or less sensitive, commensurate with the ambient surroundings.

When the reference APD 36 breaks down, an analog-to-digital converter (ADC) 44 converts the resulting anode voltage into a digital value, equivalent to the breakdown voltage. The AD converter converts the anode voltage after the avalanche current has decayed through the diode (there is no current flowing outside the diode during the breakdown). The current inside the diode discharges the diode capacitance and thus leads to a voltage drop at the anode (the cathode is pinned to a fixed voltage level, while the anode is left floating by leaving the reset transistor open). The internal current stops flowing when the voltage over the diode has reached the breakdown voltage, below that voltage, there is no multiplication possible and therefore most of the current stops and only a tiny leakage current continues to discharge the diode. The signal is processed and changed back into an analog signal by a digital-to-analog converter (DAC) 46, and is used to adjust a variable voltage source 48 that reverse biases the sensor APDs 34 and the reference APDs 36. The avalanche current, which is in the order of $10^6$ electrons per photon, will continue to flow until the voltage over the diode has reached the breakdown voltage. The time for this to happen is typically 200-300 ps depending on the excess voltage, diode capacitance and internal resistance. After that, there is no current flowing and the anode voltage reflects the breakdown voltage. This steady-state anode voltage is measured by the AD converter and the bias voltage is adjusted so that the anode voltage equals the logic level. A recharge transistor 50 is used to charge the diode back above the breakdown voltage for the next measurement cycle. That recharge pulse is about 10-15 ns long while the time to the next discharge can be in the millisecond range. A more detailed discussion of the bias control loop 42 is undertaken hereinbelow, in reference to FIG. 4.

With continuing reference to FIG. 3, a second, temperature control loop 52 is illustrated. The digital pulses from the ADC 44 are counted by a dark pulse counter 54 within a predetermined time period. Alternately, the dark pulse counter 54 could detect and count the activity of the recharging circuit 50. The dark pulse counter 54 outputs a digital value representative of the dark count rate. As temperature is proportional to the dark count rate, a driver 56 uses the dark count rate to drive a primary temperature control element 58, such as a Peltier cooling element, to quickly fine-tune the operating temperature of the APDs 34, 36. A secondary cooling element 60, which can use water, air, or other coolants, can be used to remove heat from the system. Limiting temperature variance is desirable to to limit the variance of the temperature in order to always get the same number of counts per photon.

Figure 4:
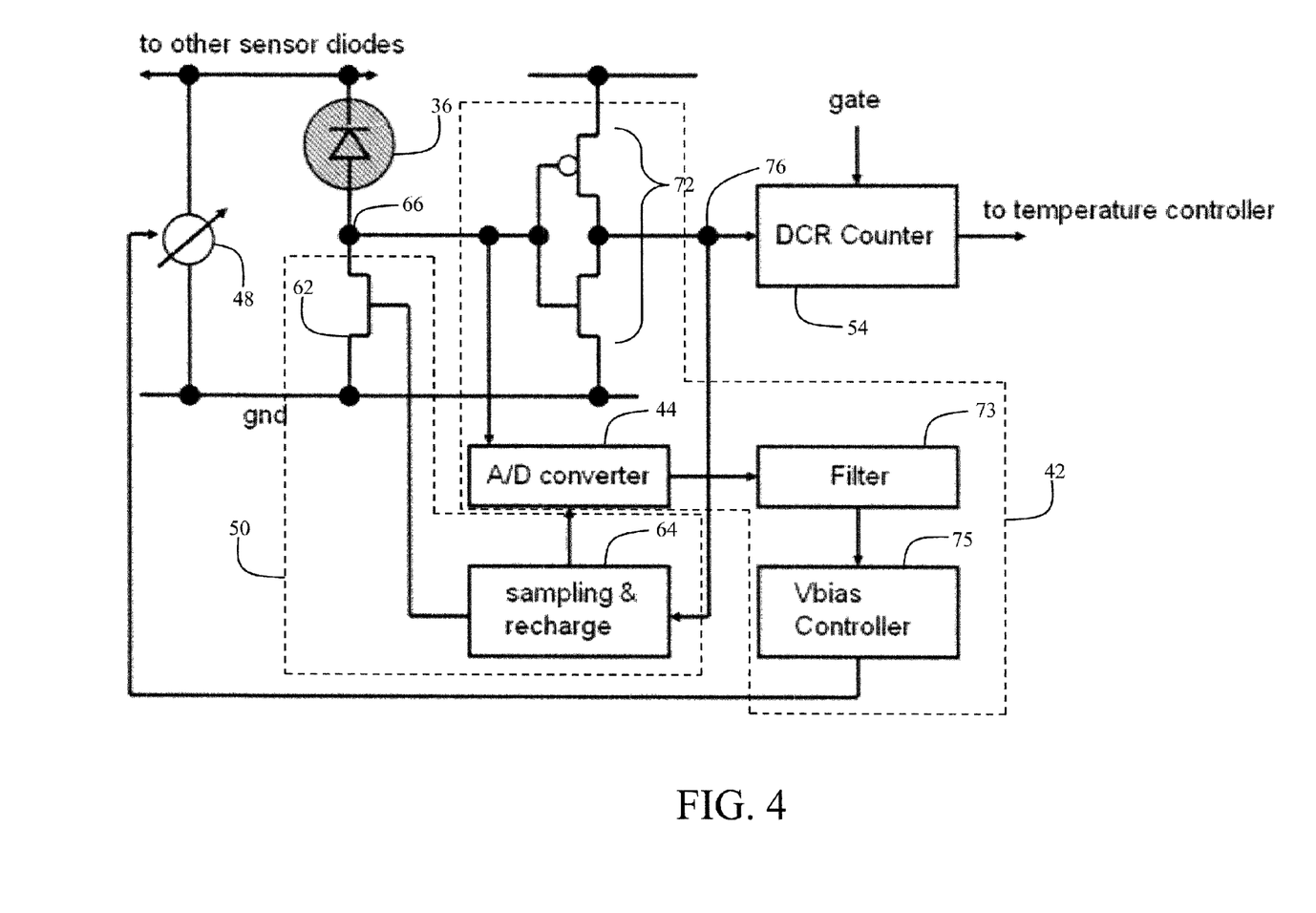
FIG. 4 shows certain circuit components used to realize the feedback loops of FIG. 3.
Figure 5:
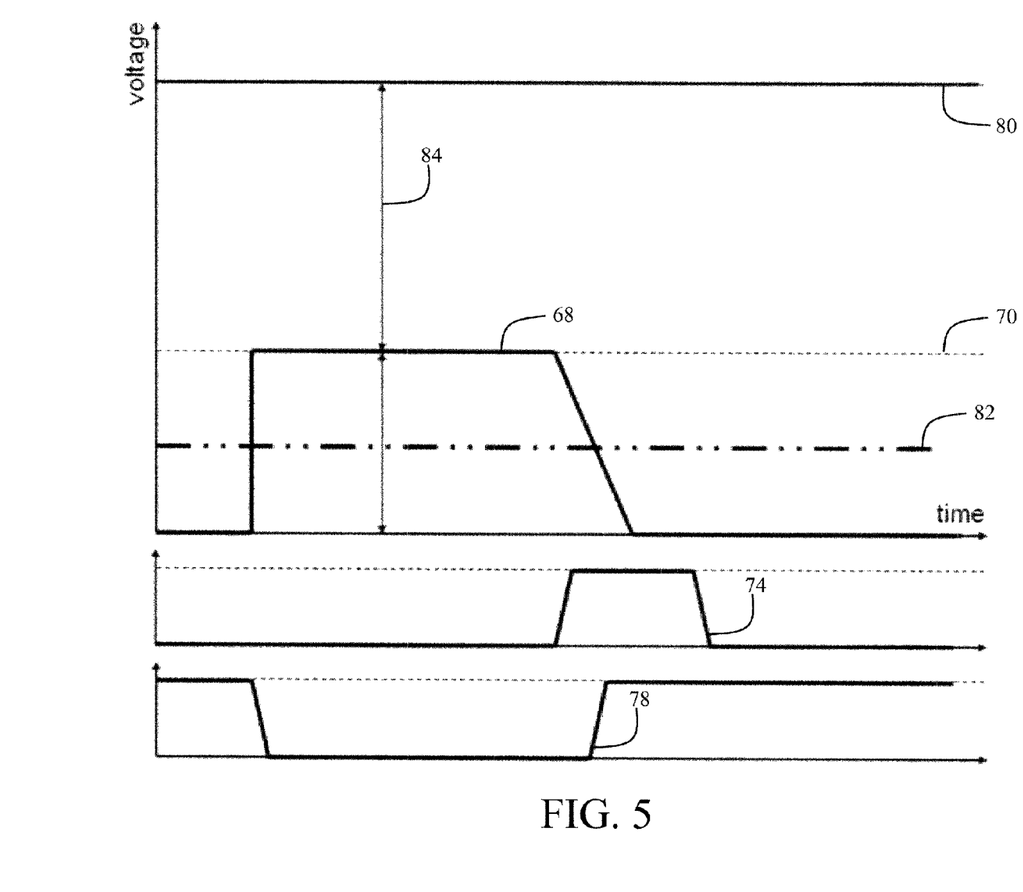
FIG. 5 depicts waveforms detailing one cycle of the circuits of FIGS. 3 and 4, with an accurate bias voltage.

With reference now to FIG. 4, the reference APD 36 is reverse biased with the variable voltage source 48. The anode is connected to a transistor 62 that is used to recharge the reference APD 36 to a selected voltage over the reference APD's 36 breakdown voltage. This is done by applying a short pulse to the gate of the transistor 62 with sampling and recharge circuitry 64, allowing the transistor 62 to turn it conductive. In one embodiment, the transistor 62 is an NMOS transistor. After this recharge, the reference APD 36 is left sensitive to carriers and will eventually break down. With reference to FIG. 5 and continuing reference to FIG. 4, during breakdown, the voltage at node 66 increases rapidly from zero, forming a voltage pulse 68, to a voltage dictated by the current operating conditions of the module 16. It is desirable for this voltage to be as close to a logic voltage level 70 as possible. The voltage pulse 68 is sensed by an inverter 72, which digitizes and passes the signal to the sampling and recharge circuitry 64, and the dark rate counter 54. The sampling and recharge circuitry 64 starts the ADC 44 to measure the actual voltage after the pulse 68 over the broken-down reference APD 36. Once the measurement is complete, the measurement is filtered 73 and passed to the bias voltage control feedback loop 42. More specifically, a bias voltage controller 75 controls the voltage output of the variable voltage source 48, described in more detail below. Additionally, the sampling and recharge circuitry 64 applies a pulse 74 that recharges the reference APD 36 resetting it so that it is once again sensitive to carriers. While the reference diode 36 is broken down, the voltage at node 76 drops to zero, as indicated by the waveform 78.

If the voltage pulse 68 is equal to the logic voltage level 70, then the bias voltage 80 is on target. Thus, a bias voltage control signal 82 produced by the bias control feedback loop 42 is correct, that is, half of the logic voltage level 70. If the bias voltage 80 is on target, no corrections are needed.

Figure 6:
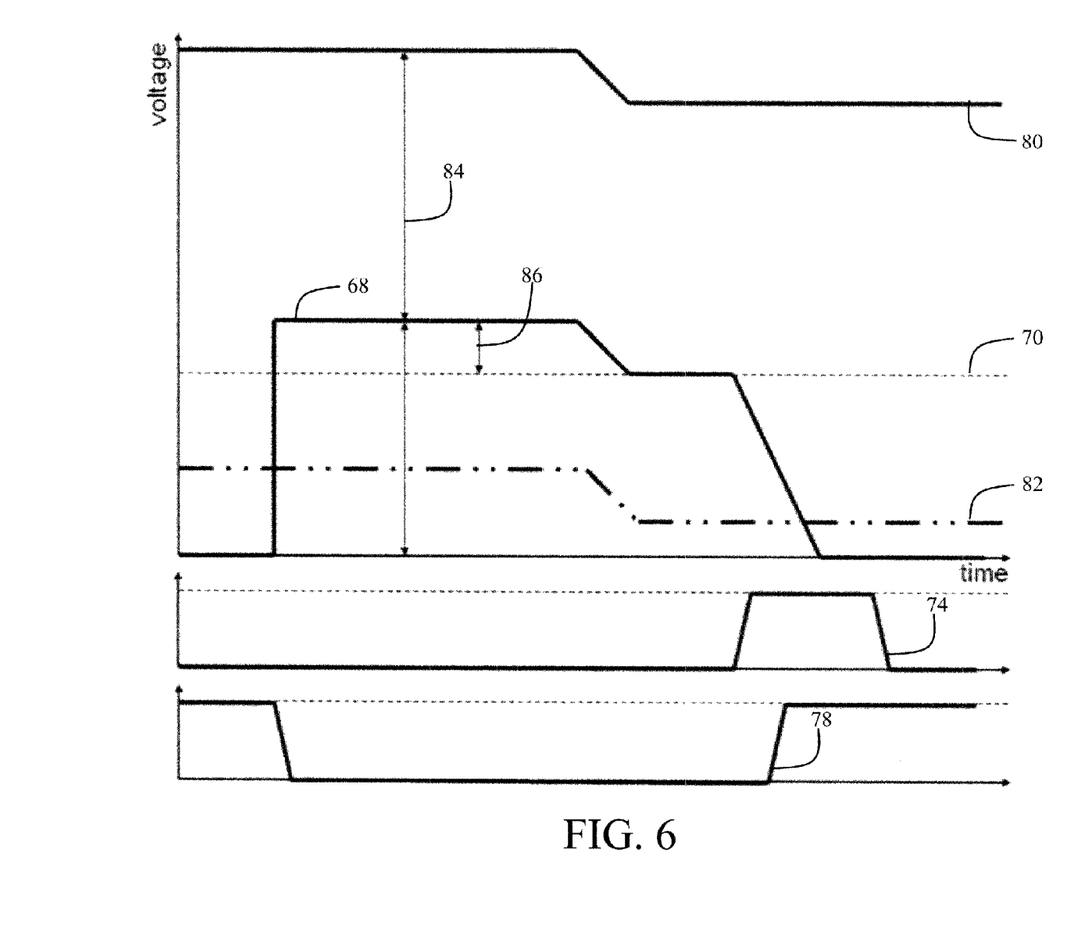
FIG. 6 depicts waveforms detailing one cycle of the circuits of FIGS. 3 and 4, with a bias voltage that is too high.

FIG. 6 depicts a situation in which the bias voltage 80 is too high, and is corrected. Such a situation may be caused by a shift in the breakdown voltage 84 of the APDs 34, 36 brought about, for example, by a lower ambient temperature. In this case, the voltage measured by the ADC 44 (i.e. the voltage of pulse 68) exceeds the logic voltage level 70 by a difference 86. In this situation, the bias control feedback loop 42 directs the variable voltage source 48 to lower the bias voltage 80, thus minimizing the difference 86 between the voltage pulse 68 and the logic voltage level 70. As in the previous example of FIG. 5, the sampling and recharge circuitry 64 applies the pulse 74 resetting the reference APD 36.

Figure 7:
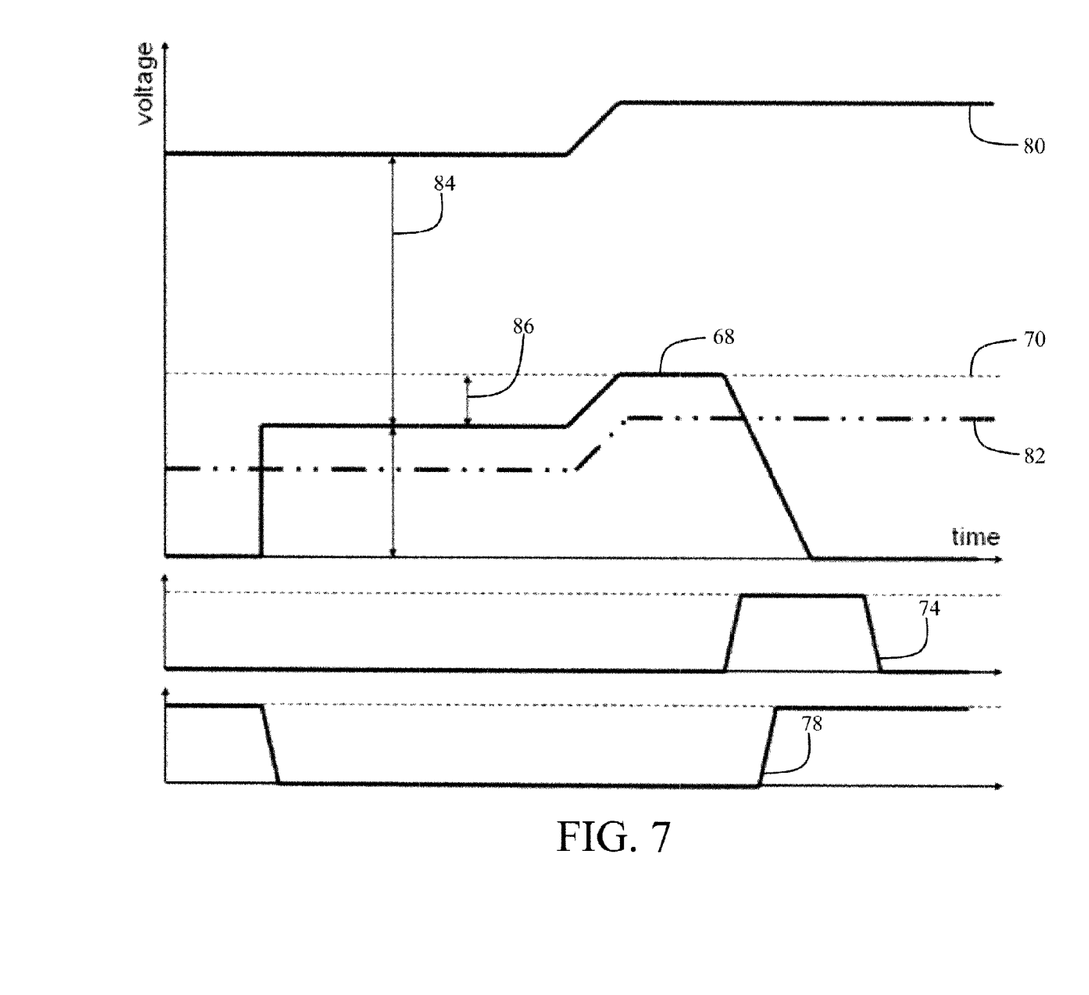
FIG. 7 depicts waveforms detailing one cycle of the circuits of FIGS. 3 and 4, with a bias voltage that is too low.

Similarly, FIG. 7 depicts a situation in which the bias voltage 80 is too low. Such a situation may be caused by a higher ambient temperature. In this case, the voltage measured by the ADC 44 (i.e. the voltage of pulse 68) is less than the logic voltage level 70 by the difference 86, which is now a negative value. In this situation, the bias control feedback loop 42 directs the variable voltage source 48 to raise the bias voltage 80, again minimizing the difference 86 between the voltage pulse 68 and the logic voltage level 70. Again, the sampling and recharge circuitry 64 applies the pulse 74 resetting the reference APD 36. In the illustrated embodiments, the bias voltage correction is done while the reference APD 36 is in its broken-down state. This allows the ADC 44 to monitor the difference 86 in real time.

In one embodiment, the circuitry depicted in FIGS. 3 and 4 can be integrated on the same die next to the APDs 34, 36 if the bias voltage is generated by a charge pump on the chip and enough chip area is available. Parts of the circuitry can be located on separate chips, thus allowing application in conjunction with analog silicon photomultipliers.

In an alternate embodiment, the bias control loop 42 can be implemented in a purely analog way, eliminating the ADC 44 and the DAC 46. In this embodiment, the reference photodiode 36 is operated at the breakdown voltage by impressing a well defined current (about 1 μA) and using the resulting voltage as a control signal for the variable voltage source 48. This embodiment would have the advantage of making the overall circuit more compact. In the digital embodiments, the ADC 44 can also be re-used to monitor other voltages. This can be useful for functional and parametric testing at the wafer level, and during the power-on sequence of the sensor module.

The present application has been described with reference to the preferred embodiments. Modifications and alterations may occur to others upon reading and understanding the preceding detailed description. It is intended that the present application be construed as including all such modifications and alterations insofar as they come within the scope of the appended claims or the equivalents thereof.

Having thus described the preferred embodiments, the invention is now claimed to be:

1. A radiation detector module for use in imaging comprising:
    a plurality of detector pixels, each detector pixel including a scintillator optically coupled to at least one sensor photodiode operated in a Geiger mode;
    at least one reference photodiode shielded from light that is operated in the Geiger mode under the same conditions as the at least one sensor photodiode;
    a control circuit that:
        measures a breakdown voltage across the reference photodiode of dark current pulses generated by the reference photodiode when the reference photodiode breaks down;
        adjusts a bias voltage across the at least one reference photodiode and the at least one sensor photodiode to bring the dark current pulses generated by the at least one reference photodiode into substantial equality with a preselected characteristic logic voltage level.

2. The radiation detector module as set forth in claim 1, further including:
    a primary cooling element thermally coupled to the at least one sensor photodiode and the at least one reference photodiode for removing heat from the at least one sensor photodiode and the at least one reference photodiode.

3. The radiation detector module as set forth in claim 1, wherein the dark current pulses are digital pulses with an amplitude of the breakdown voltage, such that the control circuit adjusts the bias to hold the amplitude of the dark current pulses and an amplitude of the at least one sensor photodiode substantially equal to the preselected logic voltage level.

4. The radiation detector module as set forth in claim 1, wherein the bias voltage biases the at least one reference photodiode and the at least one sensor photodiode into a breakdown region.

5. The radiation detector module as set forth in claim 1, further including;
    a dark pulse counter that counts dark current pulses generated by the at least one reference photodiode.

6. The radiation detector module as set forth in claim 2, further including:
    a temperature controller that controls the primary cooling element based on a frequency of detected dark current pulses from the at least one reference photodiode as reported by a dark pulse counter that counts dark current pulses generated by the at least one reference photodiode dark pulse counter.

7. The radiation detector module as set forth in claim 5, wherein the dark pulse counter identifies and counts the dark current pulses of the characteristic logic voltage level as dark current pulses.

8. The radiation detector module as set forth in claim 1, wherein the control circuit includes:
    an analog-to-digital converter that measures the breakdown voltage of the at least one reference photodiode; and
    a bias voltage controller which adjusts the bias across the at least one reference photodiode and the at least one sensor photodiode in accordance with a difference between the measured breakdown voltage and the preselected characteristic logic voltage.

9. The radiation detector module as set forth in claim 1, wherein the control circuit includes an inverter that:
    senses dark current pulses generated by the at least one reference photodiode;
    digitizes the dark current pulses;
    propagates the digitized dark current pulses to a sampling and recharge controller, which directs an analog-to-digital converter to measure the voltage of the dark current pulses.

10. The radiation detector module as set forth in claim 9, wherein the control circuit includes a recharge transistor that turns conductive upon receiving a signal from the sampling and recharge controller, returning the reference photodiode to a non-broken-down state.

11. The radiation detector module as set forth in claim 10, further including:
a dark pulse counter that counts reset pulses generated to reset the at least one reference photodiode into the Geiger mode.

12. The radiation detector module as set forth in claim 8, wherein the control circuit includes a bias voltage controller that directs a variable voltage source to adjust the bias voltage based on the measured breakdown voltage by the analog-to-digital converter.

13. An imaging apparatus comprising:
a gantry defining an imaging region;
a subject support for supporting a subject that selectively translates into and out of the imaging region;
a detector array that includes a plurality of detector modules as set forth in claim 1;
an event verification processor that analyzes detected radiation to determine whether the detected radiation originated from valid events;
an event storage buffer for storing events validated by the event verification processor;
a reconstruction processor that reconstructs valid events into an image representation.

14. The radiation detection module as set forth in claim 1, wherein the control circuit further includes:
a sampling and recharge controller which, in response to each dark current pulse, recharges the at least one reference photodiode to a non-broken-down state, resetting the at least one reference photodiode to the Geiger mode.

15. A method of compensating for drift in a sensitivity of a portion of a radiation detector array comprising:
applying a bias voltage to a plurality of sensor photodiodes and a parallel connected reference photodiode, the bias voltage biasing the photodiodes to a Geiger mode and sensitive to single photons;
following breakdown of the reference photodiode, measuring a breakdown voltage of the reference photodiode;
determining a difference between an amplitude of a digitized voltage pulse from the reference photodiode generated in response to the breakdown and a logic voltage level;
adjusting the bias voltage to minimize the difference, the bias voltage being greater than the logic voltage level.

16. The method as set forth in claim 15, further including:
preventing the reference photodiode from receiving light.

17. The method as set forth in claim 15, wherein the steps of measuring, determining, and adjusting occur during a time period when the at least one reference photodiode is in a broken-down state, and further including:
resetting the at least one reference photodiode.

18. The method as set forth in claim 15, further including:
adjusting a temperature of the reference photodiode based on how often the referenced photodiode digitized voltage pulses occur, thereby changing the breakdown voltage of the reference photodiode, to minimize the difference.

19. A non-transitory computer readable medium having stored thereon computer executable instructions for performing the method as set forth in claim 15.

* * * * *